United States Patent
Zhang et al.

(10) Patent No.: US 7,998,094 B1
(45) Date of Patent: Aug. 16, 2011

(54) SYSTEM AND METHOD OF MICROSCOPIC IMAGING AND SOFT TISSUE TENSION MEASUREMENTS

(75) Inventors: Li-Qun Zhang, Wilmette, IL (US); Yi-Ning Wu, Chicago, IL (US); Yupeng Ren, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 144 days.

(21) Appl. No.: 12/426,012

(22) Filed: Apr. 17, 2009

Related U.S. Application Data (60) Provisional application No. 61/046,038, filed on Apr. 18, 2008.

(51) Int. Cl.
*A61B 5/103* (2006.01)
*A61B 5/117* (2006.01)

(52) U.S. Cl. .......................... 600/587; 600/595

(58) Field of Classification Search ................ 600/587, 600/546, 547, 554, 595; 73/379.01; 702/127, 702/138–172
See application file for complete search history.

(56) References Cited

OTHER PUBLICATIONS

Lieber et al., "Spasticity Causes a Fundamental Rearrangment of Muscle-Joint Interaction," *Muscle& Nerve*, vol. 25, Issue 2, pp. 265-270, Jan. 28, 2002.
Fridén et al., "Spastic Muscle Cells Are Shorter and Stiffer Than Normal Cells," *Muscle & Nerve*, vol. 27, Issue 2, pp. 157-164, Jan. 14, 2003.
Hilgetag et al., "Exploring the Folds of the Brain—And Their Links to Autism," *Scientific American*, Feb. 2009.

*Primary Examiner* — Jeffrey G Hoekstra
(74) *Attorney, Agent, or Firm* — Drinker Biddle & Reath LLP

(57) ABSTRACT

An apparatus and method for examining fiber tension, fiber stress, sarcomere length, etc. in muscle fibers and tension and stress in ligament or tendon tissues as well as brain or nerve fibers by applying a lifting force to lift the fiber or tissue a lifting distance, measuring the lifting force and distance and calculating the axial tension on the fiber bundle or tissue. The apparatus and method also make it possible to illuminate and view the fiber bundle or tissue to examine and characterize visually observable properties.

6 Claims, 8 Drawing Sheets

SYSTEM AND METHOD OF MICROSCOPIC IMAGING AND SOFT TISSUE TENSION MEASUREMENTS

FIELD OF THE INVENTION

This invention relates to imaging and measurement of tissue features and, more particularly, to a system and method for examining in vivo biomechanical properties like fiber tension, fiber stress, sarcomere length and number of sarcomeres in series of single muscle fibers or small bundles of muscle fibers as well as biomechanical properties of other soft tissues like ligament, tendon, brain and nerve tissue.

BACKGROUND OF INVENTION

Spasticity, contracture, and muscle weakness commonly occur in conjunction with various neurological disorders such as stroke, spinal cord injury, poliomyelitis, cerebral palsy, amyotrophic lateral sclerosis, multiple sclerosis, muscular dystrophy, myasthenia gravis, and spinal muscle atrophy. These symptoms of spasticity, contracture, and muscle weakness are closely related to each other and are major factors contributing to disabilities in patients with such neurological impairments. If a method were available for determining in vivo biomechanical properties like fiber stress, fiber force, fiber tension, sarcomere length, sarcomere uniformity/non-uniformity, and number of sarcomeres in series of single muscle fibers or small bundles of muscle fibers, diagnosis and treatment of these symptoms could be substantially improved. If such a system could be used to determine in vivo biomechanical properties of other soft tissues such as ligament or tendon tissues, or brain or nerve fibers/axons, the functioning of these tissues could be more effectively analyzed and advancements in diagnosis and treatment of symptoms associated with injuries and impairments in such tissues also could be significantly advanced. For example, if the level of stress in externally accessible nerve fibers in the brain could be determined in vivo, it may be possible to better diagnose and treat neural-based maladies related to disturbances in the network of nerve fibers that pull the cortex into shape during brain development and hold it in place throughout life.

Current methods of examining properties of muscle fibers like fiber stress, sarcomere length and number of sarcomeres in series are inaccurate and unreliable because they must be performed in vitro and because they rely on methods like laser diffraction which yield only average sarcomere fiber length data. Most importantly, in vitro sarcomere length measurements have been shown to differ significantly from actual in vivo sarcomere lengths. Also, laser diffraction measurement of sarcomere length relies upon the production of diffraction lines produced by passing laser light through muscle fibers to produce a diffraction pattern from which average sarcomere lengths over a substantial area taking in a multiplicity of fibers and sarcomeres can be derived. The laser diffraction technique therefore does not permit precise determination of the length of selected sarcomeres in small isolated muscle fibers or fiber bundles and offers no opportunity for actually viewing and determining the lengths of the sarcomeres in muscle fibers of interest.

A system for examining in vivo biomechanical properties like fiber stress, sarcomere length and number of sarcomeres in series of single muscle fibers or small bundles of muscle fibers could lead to breakthroughs in the diagnosis and treatment of such neuromuscular disorders by demonstrating, inter alia, whether spastic fibers are under higher stress as compared to those of healthy subjects and the level of such stress, and whether sarcomeres in spastic muscles adapt to increased tension by adding more sarcomeres in series as in normal cases. If it were possible to examine sarcomere lengths at rest and under tension in vivo in a meaningful and reliable way, this would help guide and optimize treatment. In order to do this it is important to have accurate and economic methods and apparatus. The present invention provides such apparatus and methods for determining fiber stress, sarcomere length and number of sarcomeres in series under in vivo conditions. The present invention also provides apparatus and methods for determining tension and stress of collagen or other fibers as well as fiber arrangement in other soft tissue such as ligament, tendon tissues, and in brain and nerve fibers/axons.

SUMMARY OF THE INVENTION

In one embodiment, the invention comprises an apparatus for examining muscle tissue features. The apparatus includes a fiber bundle support for applying a lifting force to a muscle fiber bundle having an initial length to lift the fiber bundle a lifting distance. The apparatus also includes means for measuring the lifting the force and means for measuring the lifting distance. From the initial length, lifting force and lifting distance the axial tension on the fiber bundle can be calculated in accordance with the invention by solving for the tension value from equations which relate to these and other parameters. The equations are set forth below.

The apparatus of the invention also includes means for illuminating at least a portion of the fiber bundle or tissue subjected to the lifting force and means for viewing the illuminated portion of the fiber bundle. For example, the fiber bundle may be illuminated by a fiber optic illuminator and a fiber optic light guide. The image may be picked up by a CCD camera and displayed on video display.

One method of the invention begins with exposing a fiber bundle in the body of a muscle of a living subject and separating the bundle from the body of the muscle. The fiber bundle will have an initial fiber bundle length $x_0$. Then, a lifting force $F_y$ is applied to the bundle to pull it away from the body of the muscle a lifting distance y. Finally, the axial tension on the fiber bundle will be calculated based on the initial length, lifting force and a lifting distance. These calculations will be performed using equations relating the measured parameters as set forth below.

The apparatus and method of the invention may be used, as well, for determining in vivo biomechanical properties of other soft tissues such as ligament or tendon tissues, or brain or nerve fibers/axons.

BRIEF DESCRIPTION OF THE DRAWINGS

The features of this invention that are believed to be novel are set forth with particularity in the appended claims. The invention, together with its objects and advantages, may be best understood with reference to the following description, taken in conjunction with the following drawings, in which like reference numerals identify like elements in the figures, and in which:

DETAILED DESCRIPTION OF PREFERRED EMBODIMENTS OF THE INVENTION

The embodiments of the invention described in detail below are not intended to be exhaustive or to limit the invention to the precise structures and methods disclosed. Rather, the described embodiments have been chosen to explain the principles of the invention and its application, operation and use in order to best enable others skilled in the art to follow its teachings.

Method

Figure 6:
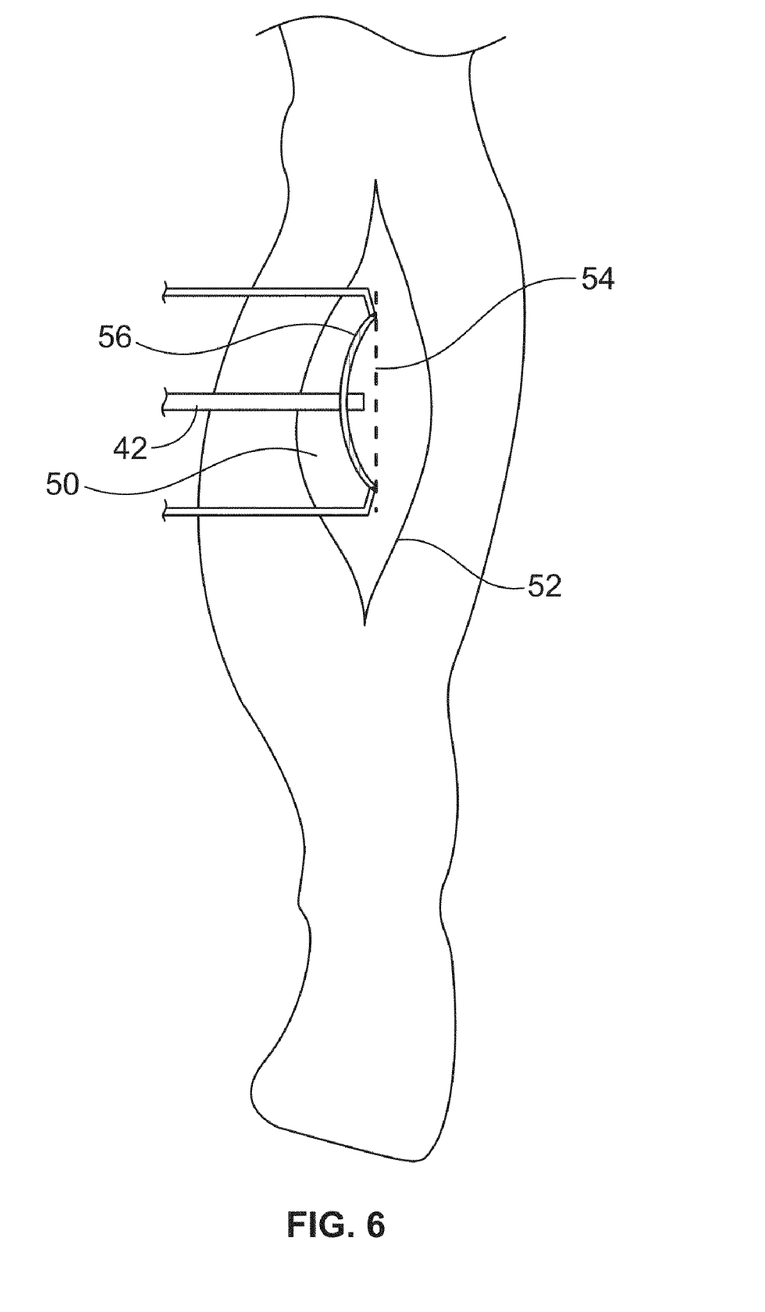
FIG. 6 shows a portion of a tibialis anterior muscle exposed within operative field 5, for examination of the properties of a muscle fiber bundle.

A method of the present invention entails:

A. Exposing a fiber bundle in a living subject (animal or human) by making an appropriate incision in the skin over the muscle region of interest (e.g., deltoid, biceps brachii, triceps brachii, quadraceps, peroneus longis, brachioradialis, hamstring, soleus, flexor carpi ulnaris, gastrocnemius, or tibialis anterior) (Step 10). See also FIG. 6.

B. Teasing away a small muscle fiber bundle (e.g., about 10 mm long, 1 mm wide and 0.4 mm or less deep) to separate it from the body of the muscle. (Step 12). The bundle should be thin enough to allow light generated in the apparatus of the invention to penetrate through the bundle.

C. Pulling the bundle away from the body of muscle a measurable distance by applying a lifting force at or near the midpoint of the bundle using a micrometer, a motorized stage, or other appropriate device. (Step 14). While lifting at the midpoint of the fiber bundle is preferred because it involves simplified calculations and yields accurate results when used in the calculations described below, the lifting may be done at other points along the fiber bundle using more complex but readily derivable calculations.

D. Measuring the lifting force and the distance the bundle midpoint is moved off of the underlying muscle. (Step 16).

E. Calculating the axial tension on the fiber bundle as explained below. (Step 18).

F. Optionally displaying the sarcomeres of the fiber bundle as they appear at steps B, C and D on a video display at the desired magnification. (Step 20). Muscle fibers under tension usually increase the number of sarcomeres in series. However, some neurological conditions may impair this process, so that muscle fibers under increased tension do not have a sufficient number of sarcomeres in series. Sarcomeres in this case may become considerably elongated. At the muscle fascicles level, this may be manifested as stiff muscle fascicles. At the joint level, it may be manifested as stiff and/or spastic joint. Thus, displaying the sarcomeres of the fiber bundle as noted will help understand pathological changes in the muscle (e.g., changes in quantity of sarcomeres or changes in sarcomere length) to aid choosing and designing an appropriate treatment and to help in evaluating the efficacy of treatments that are implemented.

The Calculation

Figure 1:
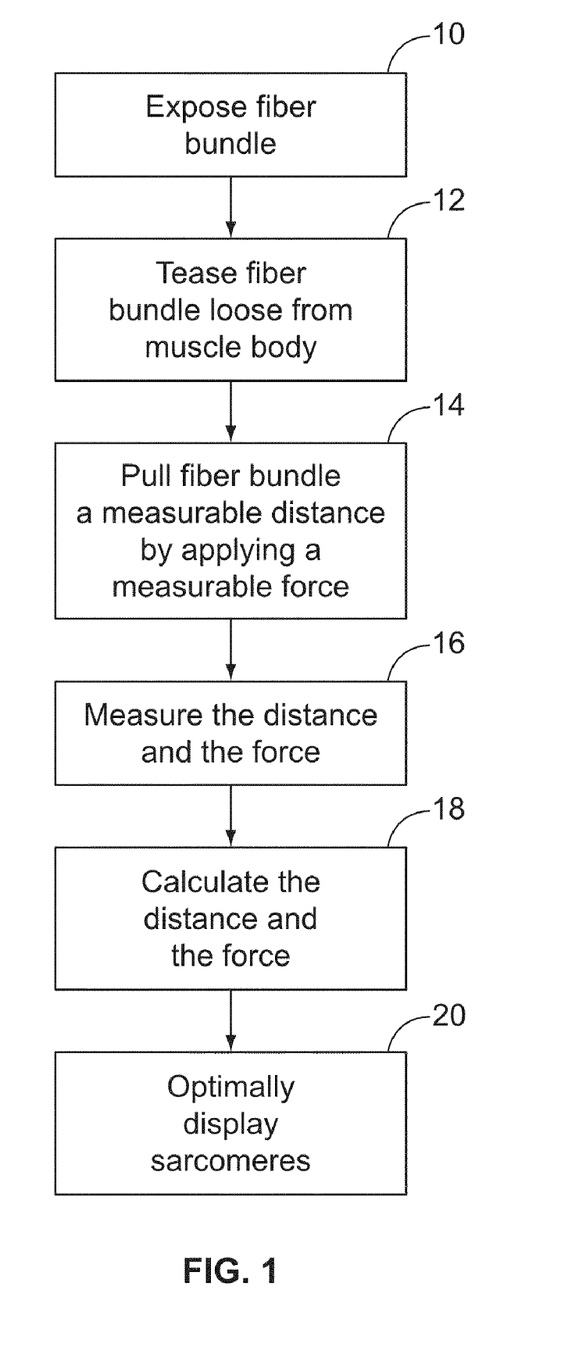
FIG. 1 is a block diagram broadly illustrating the method of the invention.
Figure 2:
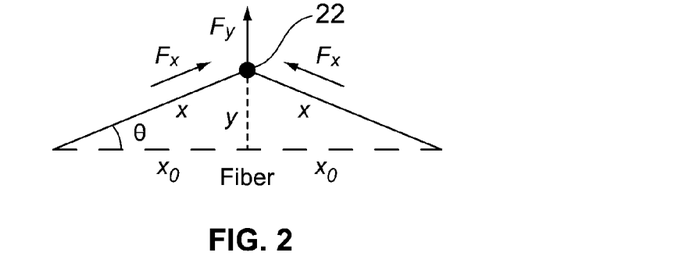
FIG. 2 is a diagrammatic representation of the relationship between the axial tension lifting force on a fiber bundle.

The fiber bundle preferably will be lifted at its midpoint 22 as illustrated diagrammatically in FIG. 2. This Figure illustrates the relationship of $F_x$, $F_y$, $x_0$, x and y equations (1) and (2), which are set forth below. The axial tension ($F_x$) along the fiber bundle is determined in accordance with the invention by applying a lifting force ($F_y$) at a lifting distance (y), using Equations (1) and (2). The lifting angle $\theta$ can be determined from the lifting distance y and half of the initial fiber bundle length $x_0$ based on Equation (2). From the measured lifting force $F_y$ and lifting angle $\theta$, the axial tension $F_x$ can be determined based on Equation (1).

$$F_x = \frac{F_y}{2\sin(\theta)} \quad (1)$$

$$\theta = \tan^{-1}\left(\frac{y}{x_0}\right) \quad (2)$$

Figure 3A:
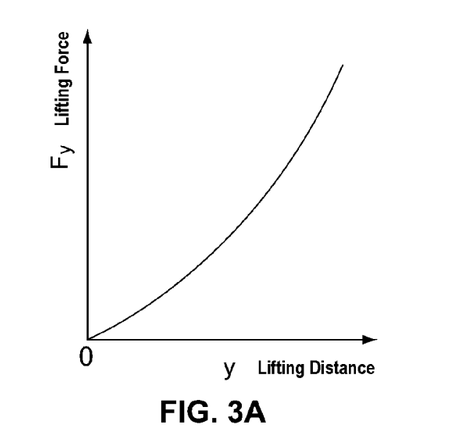
FIGS. 3A and 3B are graphs respectively illustrating measured lifting force as a function of lifting distance and axial tension as a function of fiber elongation.

The calculation preferably will be carried out using a digital computer programmed to solve for $F_x$ and $\theta$ Lifting force $F_y$ at or near the fiber bundle midpoint increases monotonically with the lifting $\theta$ distance y (which is directly related to lifting angle $\theta$) as illustrated in FIG. 3A. If needed, the lifting force can be low-pass filtered to obtain a smoother curve. Since the axial force determined at a small lifting angle $\theta$ involves a relatively large error (especially at) $\theta=0°$, the axial force preferably will be determined at a relatively large lifting angle $\theta$. Preferably, the fiber bundle will be stretched to about 150% of its original length which will correspond to a lifting angle of from about 15 to 60 degrees. Also, the fragility of the fiber bundle must be taken into account to avoid over-stretching a bundle to the point that it may not return to its original length when the lifting force is removed. The objective, of course, is to extrapolate to obtain data as close to $\theta=0°$ as possible to obtain the axial force of the bundle at rest (no lifting force $F_x$). This is because at rest, the fibers may have considerable tension which may be an indication of pathological conditions such as spasticity and/or contracture.

Figure 3B:
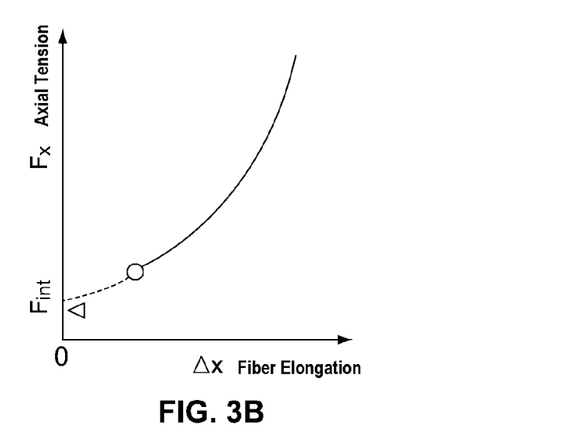

The plot of FIG. 3B indicates the estimated axial tension $F_x$ as a function of the fiber bundle elongation $$\Delta x = x - x_0 = \sqrt{x_0^2 + y^2} - x_0.$$

An exponential relationship $F_x = C_1 e^{C_2 \Delta x}$ is applied to the data to determine parameters $C_1$ and $C_2$ (FIG. 3B). $C_1$ and $C_2$ are constants/parameters characterizing the exponential curve. $C_1$ represents the fiber tension under zero elongation (when $\Delta x=0$) and $C_2$ represents the rate/slope of the exponential curve. Furthermore, the initial axial tension before lifting the fiber bundle can be determined by extrapolating the curve to the ordinate with the intercept at $\Delta x=0$ corresponding to the initial axial tension $F_{init}$ before application of the lifting force. This method can be used to predict the initial tension under various conditions.

The Apparatus

Figure 4:
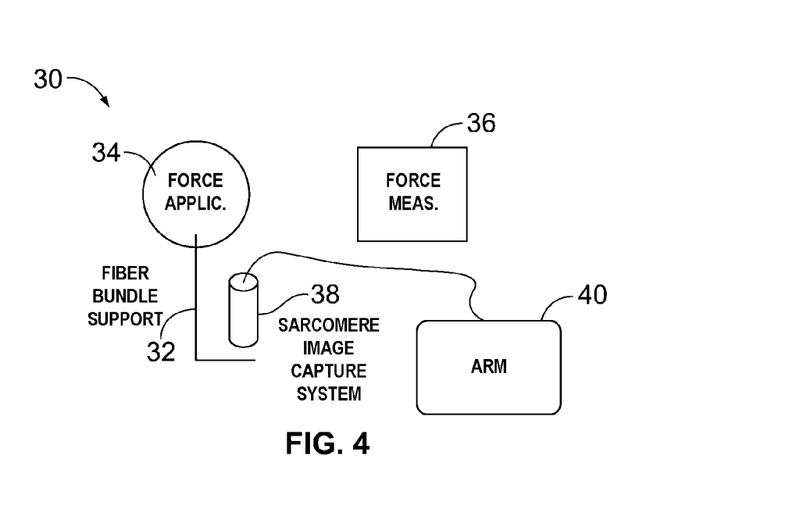
FIG. 4 is a diagrammatic representation broadly illustrating the apparatus of the invention.

An apparatus 30 in accordance with the present invention for performing the above method will include a fiber bundle support 32, a lifting force application means 34, force measuring means 36 and, optionally, a sarcomere image capture system 38 and video display 39, all as illustrated diagrammatically in FIG. 4. The details of such an apparatus 30 for measuring the force of a small bundle of fibers and sarcomere length in vivo are illustrated in FIGS. 5A-5C.

Figure 5A:
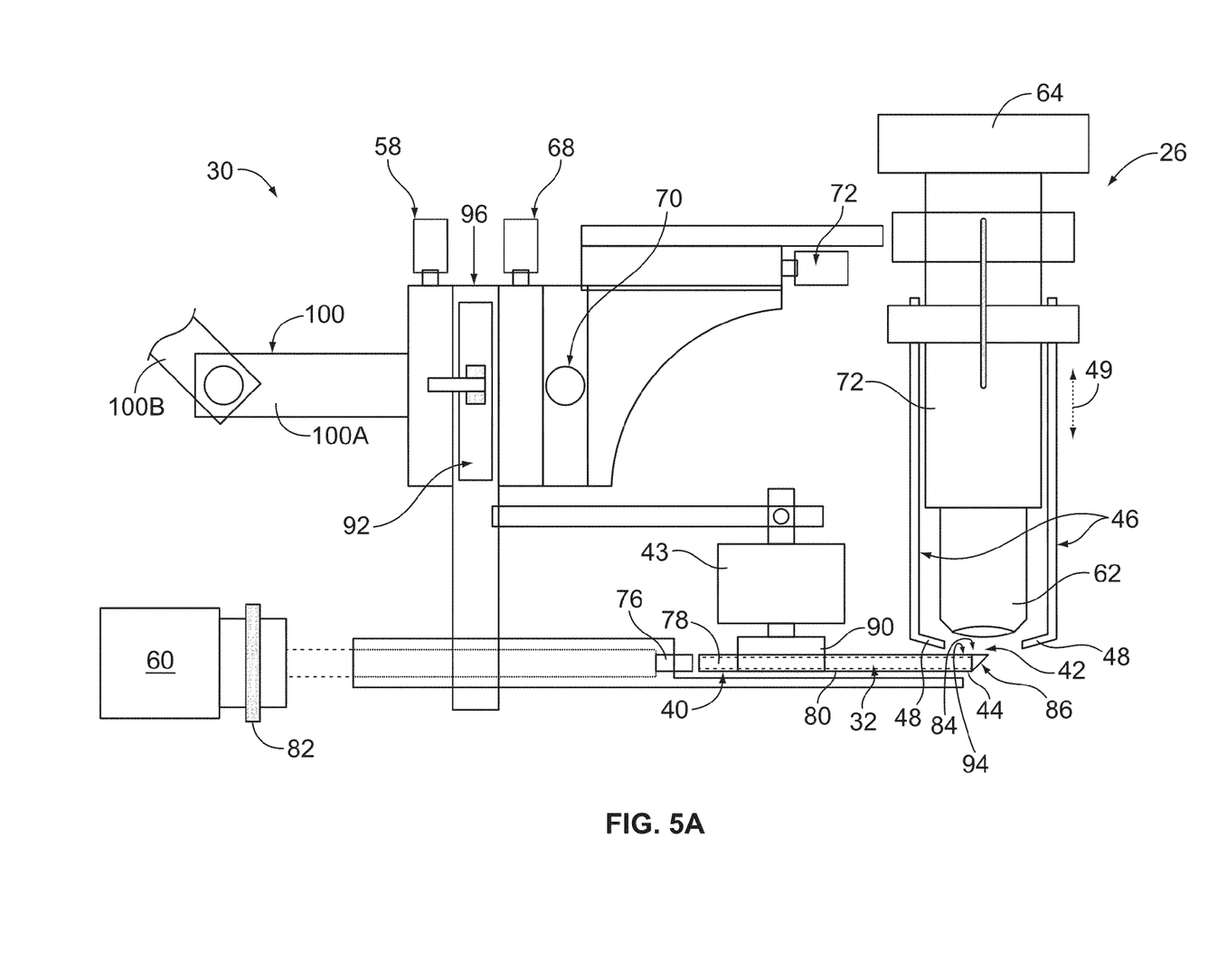
FIGS. 5A and 5B depict in detail an apparatus in accordance with the invention for evaluating muscle fiber tension and sarcomere length in vivo and FIG. 5C depicts in detail an in vitro application of the apparatus of FIGS. 5A and 5B.
Figure 5B:
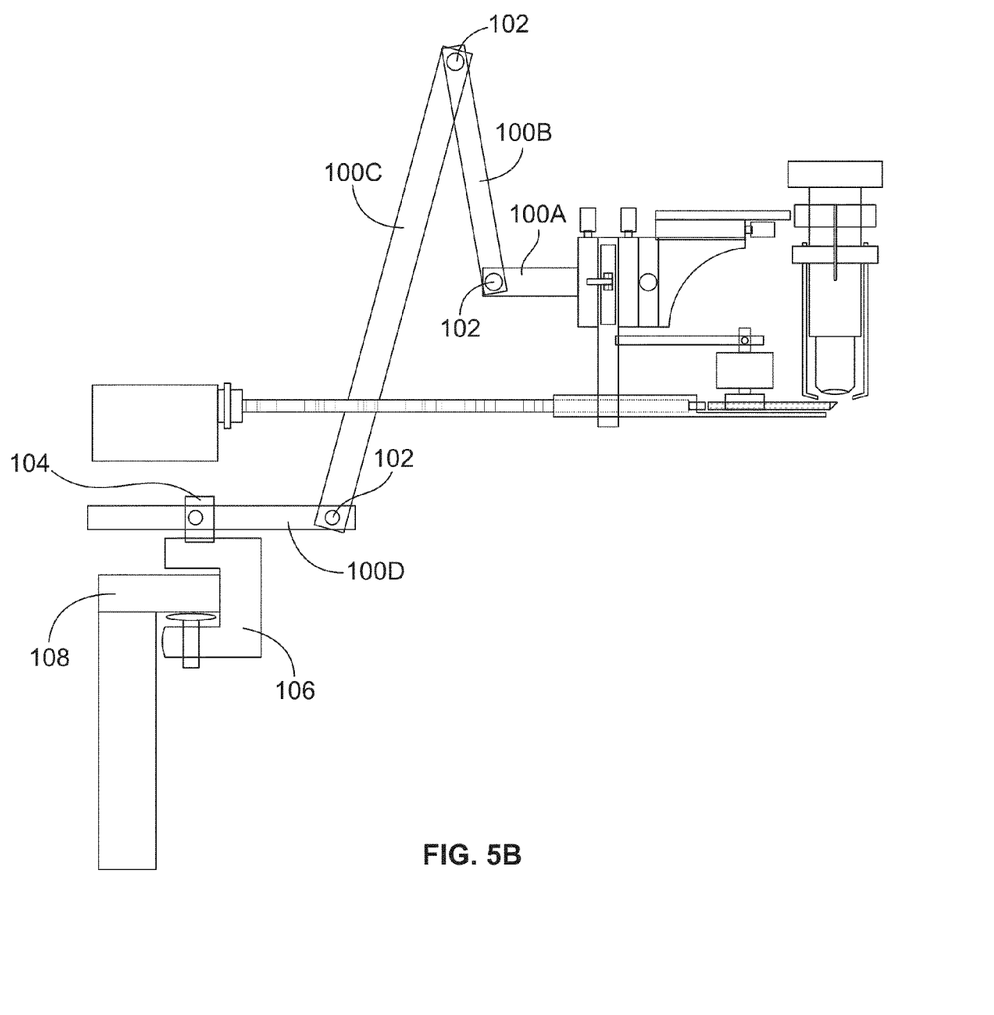
Figure 5C:
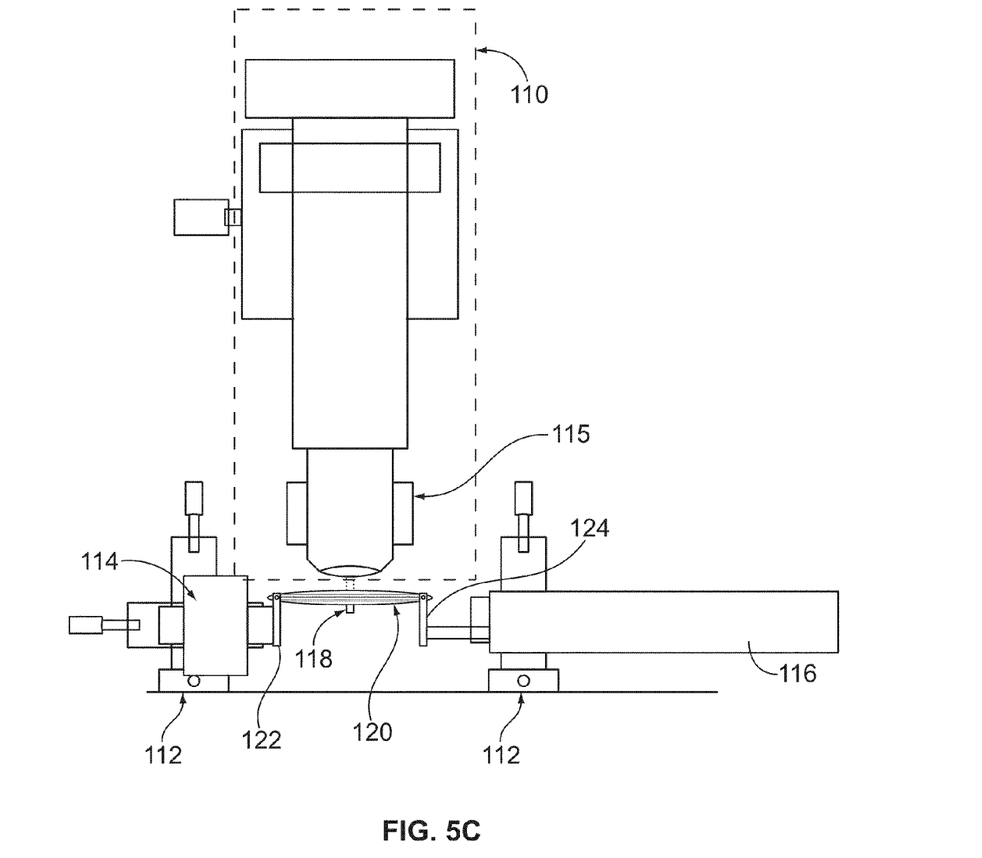

Exemplary apparatus 30 as illustrated in FIG. 5A thus includes fiber bundle support 32 consisting of a rigid arm 40 with a fiber bundle catch 42 at its distal end 44 for inserting under the exposed fiber bundle. Preferably, a pair of fingers 46 with tips 48 spaced apart a distance equal to or slightly greater than the initial fiber bundle length $x_0$ will be mounted for movement in direction 49 and locking in the desired position. Tips 48 of fingers 46 will be moved into engagement with the exposed surface of the muscle at either end of the exposed fiber bundle before being locked into place to prevent the ends from pulling away from the underlying muscle while the lifting force is applied. (The fingers are rotated 90° in FIG. 5 to better illustrate them—in the device they would be generally perpendicular to the sheet containing FIG. 5 so that the finger tips touch the exposed fiber bundle which also would be positioned generally perpendicularly to the sheet). The engagement of finger tips 48 with the exposed fiber bundle is illustrated diagrammatically in FIG. 6 with a portion 50 of a tibialis anterior muscle exposed within operative field 52 and the exposed fiber bundle at initial length 54 shown in broken lines. Catch 42 is under the bundle so that the catch pulls the fiber bundle to produce the final length 56 of the fiber bundle.

Returning to FIG. 5A, arm 40, which is mounted for vertical movement, is under control of a vertical movement control 58 constituting one embodiment of a force application means 34 as referenced above with respect to FIG. 4. As vertical movement control 58 is manipulated it lifts the fiber bundle lifting distance y away from its resting position which can be read directly from the vertical movement control or electronically converted into a digital signal that drives a digital readout. Additionally, arm 40 is provided with a force transducer 43 constituting one embodiment of a force measuring means 36. Force transducer 43 provides a measure of the tension on the muscle fiber at the chosen lifting distance y.

Apparatus 30 also includes an image capture system 26 comprising a light source 60, an objective 62, a CCD camera 64, as well as adjustable XYZ stages 66, 68 and 70. XYZ stages 66, 68 and 70 permit fine-adjustment of the focus and the field of view. Coarse-adjustment of the focus can be done by shifting lens tube 72 which is described below.

Objective 62, which is preferably about 80× magnification, includes a lens tube 72, associated with CCD camera 64. Light source 60 preferably comprises a fiber optic illuminator such as a Dolan-Jenner DC-950H fiber optic illuminator which supplies illumination to a flexible fiber optic light guide 76. Other appropriate fiber optic illuminators may be used in lieu of the DC-950H fiber optic illuminator. In the illustrated embodiment the optic light guide has diameter of about 1/16 inch although light guides of any appropriate diameter may be used. The light guide is continuously aligned but preferably not attached to an optic fiber 78 optionally embedded in a rigid tube 80. Tube 80 preferably will be made of stainless steel. The optic fiber guides the light transmission within the tube. In the light source, an iris diaphragm 82 may be used to control the light intensity to optimize the illumination and contrast of the image. Also, appropriate light filters such as polarizing filter, may be used at the light source or elsewhere in the system to optimize fiber imaging.

At the distal end 84 of tube 80, a right angle prism 86 may be used to redirect the light path by achieving a 90° or other appropriate light path bend. For example, a 0.5 mm, BK7 uncoated right angle prism available from Edmund Optics could be used. Prism 86 acts as the fiber bundle catch 42 to apply the lifting force to the fiber bundle at midpoint 22 (FIG. 2). Thus, when the distal end 84 of tube 80 is positioned beneath the fiber bundle, the fiber will be illuminated by the light directed from optic fiber 78 through prism 86 and the fiber bundle whereupon the tissue images will be magnified by objective 62 and the lens tube 72, captured by CCD camera 64 and displayed.

Tube 80 is connected to force transducer 43 through a tube holder 90. The tube holder which may be made of Delrin™ acetal resin or any other appropriate material. The tension generated by the soft tissue during lifting is measured by the force sensor. A linear position sensor 92 is attached to vertical movement control 58 to record the relative displacement y of the fiber bundle.

The light guide holder may be extended distally to prevent the soft tissue from touching the rest of the muscle or the holding tube. In this case, the tissue will touch the tube at point 94.

The light source, the force sensor and the adjustable XYZ stages are attached to a base plate 96 which is in turn mounted onto vertical movement control 58. After adjusting the focus and the field of view using the adjustable XYZ stages, the vertical movement control 58 is used to lift the fibers by raising the base plate and all the parts mounted to it while keeping the relative position of the fibers and the objective unchanged. This arrangement allows the device to be moved in 3D space to approach the target being evaluated.

The entire apparatus 30 may be removably attached to a bench or other external support means as illustrated in FIG. 5B which will permit the apparatus to be positioned and used, e.g., at an operating table if desired. This arrangement thus includes a flexible arm 100 attached to bench 108 through clamp 106. Arm 100 includes four portions, 100A, 100B, 100C and 100D interconnected by pivots 102, which can be locked at any desired position. Arm portion 100D is slidingly mounted in a locking member 104 which in turn is attached to a clamp 106 which may be removably affixed to a cart or bench 108.

FIG. 5C shows a portion of the in vivo device of FIG. 5A in a dashed-line box 110 as used to directly determine the axial force on the fiber bundle with linear motor 116 controlling the fiber bundle tension to produce controlled movement and loading of the fiber bundle with the same tension measured in two ways. This set-up includes XYZ stages 112, X coordinate force sensor 114 and Y coordinate force sensor 115, and a linear motor 116 to apply an appropriate (in vitro) stretch to a fiber bundle mounted to tips 122 and 124, as shown, before applying a lifting force to fiber bundle 118 by way of prism 118.

Examples

The following examples further illustrate the invention but, of course, should not be construed as in any way limiting its scope.

Figure 7A:
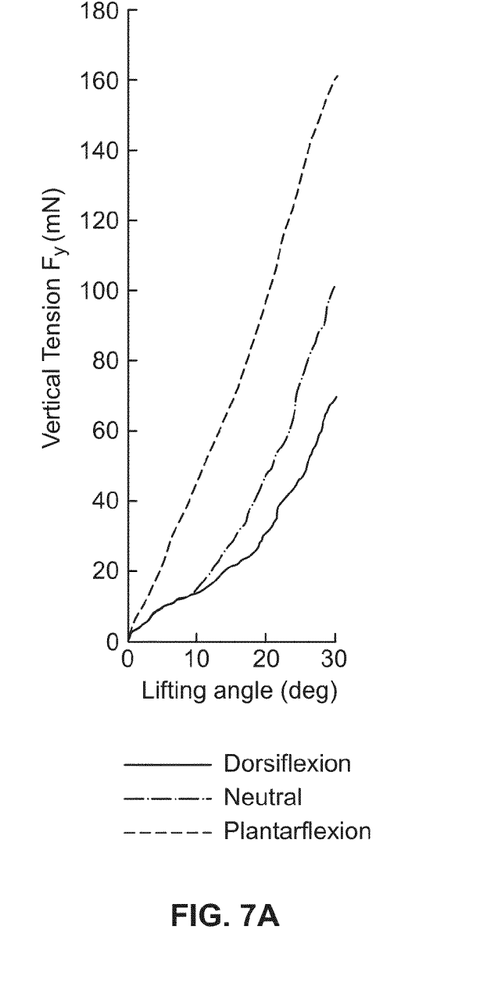
FIGS. 7A-7B pertain to the determination of axial tension from the measured lifting force and respectively show lifting force versus lifting angle, estimated axial force data fitted by an exponential equation, and in vivo stress-strain relationship of the fiber bundle.
Figure 7B:
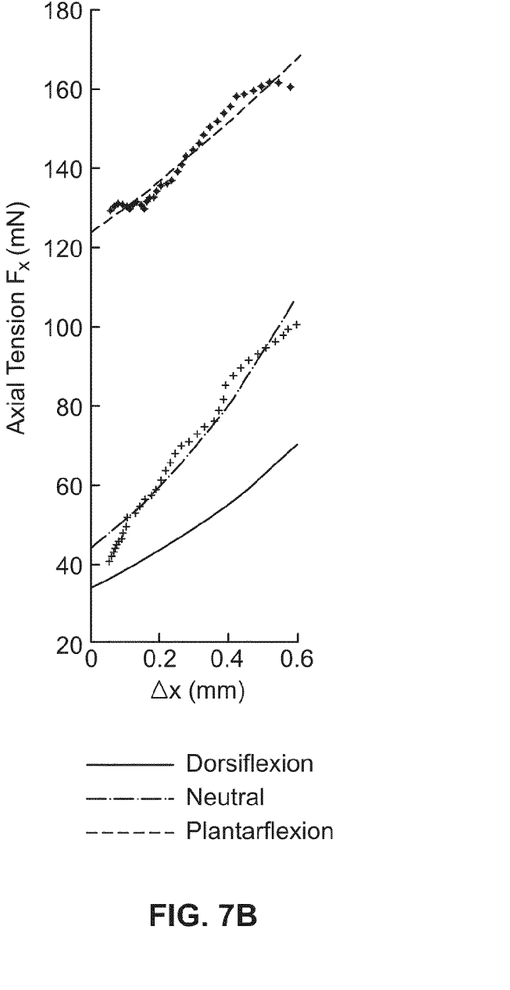
Figure 8A:
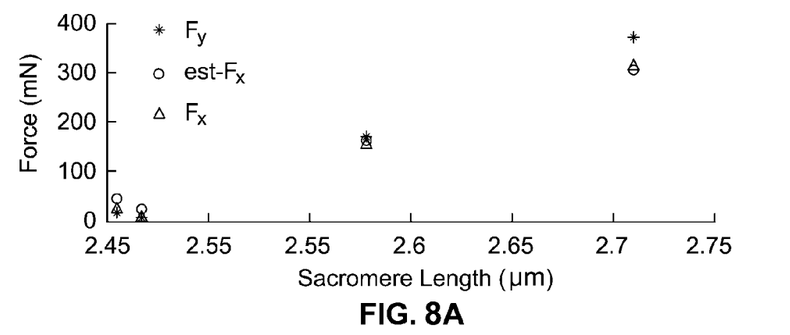
FIGS. 8A-8D are a series of plots comparing in vivo and in vitro measurements of sarcomere length.
Figure 8B:
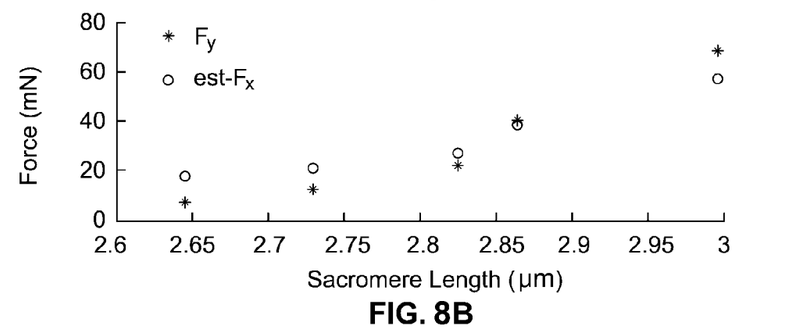
Figure 8C:
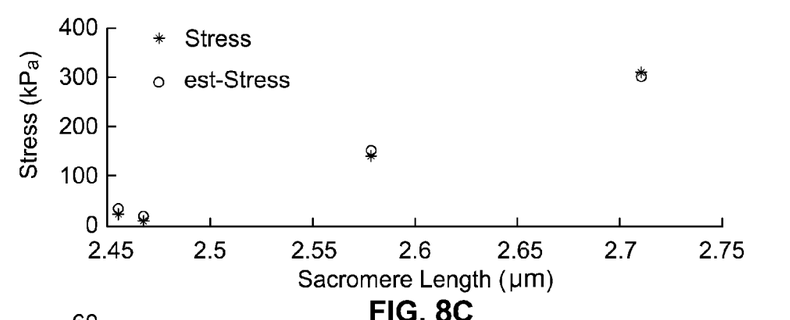
Figure 8D:
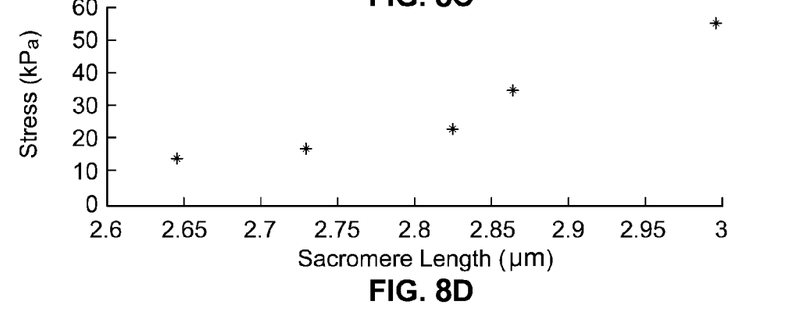

1. Tension and sarcomere length of the tibialis anterior muscle of Sprague-Dawley rats were determined in this example, with the results showing the in vivo steps relationship of the fiber bundle as depicted graphically in FIGS. 7A-7B. A small bundle of fibers was isolated with the two ends still attached to the remaining muscle bulk. The evaluation was done at the 45° dorsiflexion, neutral, and 45° plantar flexion.

The small bundle of tibialis anterior muscle fibers was lifted and the lifting force measured with the ankle held at three different positions. By substituting the measured $F_y$ into Equation (1) above, the axial force $F_x$ was determined. Since the measurement at the initial lift was difficult with $F_x$ becoming undefined at $\theta=0$ in Equation (1), the data in the range with the lifting angle was used. The axial force was curve-fit based on $F_x = C_1 e^{C_2 \Delta x}$, which was then extrapolated to $\Delta x = 0$ to determine the initial tension $F_x$ at zero lift (FIG. 3B).

From the axial force $F_x$ and cross-sectional area of the fiber bundle, fiber bundle stress was determined. From fiber bundle elongation $\Delta x$ and its initial length $x_0$, the fiber bundle strain was determined. With the width and thickness of the fiber bundle measured (e.g., 1.5 mm and 0.4 mm respectively), the stress-strain relationship was determined (FIG. 3B).

The initial axial tension of the tibialis anterior bundle was higher at plantar flexion as compared to the neutral position, which in turn was higher that that at the dorsiflexed position (FIG. 5). Furthermore, a steeper slope of the axial force versus elongation indicated higher axial stiffness. The fiber bundle became stiffer as the ankle was plantar flexed with the tibrallis anterior stretched.

2. The in vitro corroboration set-up of FIG. 5C was used to corroborate the axial force determination based on the in vivo measurement as depicted in FIGS. 8A-8D. After the in vivo measurement, the small bundle of fibers was dissected out with the two ends mounted to tips 122 and 124 of linear motor 116 and x force sensor 114, respectively.

The corroboration set-up, which included the in vivo measurement device combined with an in vitro set-up was composed of the horizontal force sensor and the linear motor. Each of them was mounted onto a set of XYZ stages for proper alignment. The specimen was loaded by the linear motor. A Labview™ program was used to control the motor and driver and acquire the data.

Microscopic images which were recorded in vivo from the fiber bundle showing visually that the sarcomere length increased with increased lifting force. This topologically relevant information will facilitate diagnosis and treatment as discussed earlier.

Finally, the in vitro experiment corroborated the in vivo measurements of the axial tension along the fiber bundle. In other words, the estimated axial force derived from the lifting force closely matched with the measured axial force.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

We claim:

1. An apparatus for examination of muscle tissue features in vivo comprising:
    a fiber bundle support for applying a lifting force to a muscle fiber bundle that has been pulled away from the body of a muscle in vivo and attached to a body at both ends having an initial length to lift the fiber bundle a lifting distance;
    a force transducer for measuring the lifting force applied to the muscle fiber bundle by the fiber bundle support;
    a position sensor for measuring the lifting distance applied to the muscle fiber bundle by the fiber bundle support; and
    a routine for calculating the axial tension on the fiber bundle based on the initial length, the lifting force applied by the fiber bundle support and the lifting distance.

2. The apparatus of claim 1 including a light source for illuminating at least a portion of the fiber bundle to which the force is applied and an image capture system for viewing the illuminated portion of the fiber bundle.

3. The apparatus of claim 1 wherein the apparatus includes a pair of fingers for engaging the fiber bundle at either end to prevent the ends of the bundle from pulling away from the underlying muscle while the lifting force is applied.

4. The apparatus of claim 2 wherein the image capture system for viewing the illuminated portion of the fiber bundle includes a fiber optic illuminator and a fiber optic light guide.

5. The apparatus of claim 1 wherein:
    the routine for calculating the axial tension $F_x$ on the fiber bundle applies the equation $$F_x = \frac{F_y}{2\sin(\theta)}$$

where $F_y$ is the lifting force applied to the bundle to pull the bundle away from the body of the muscle tissue a lifting distance y, $x_0$ is half of the initial fiber bundle length and $$\theta = \tan^{-1}\left(\frac{y}{x_0}\right).$$

6. An apparatus for examination of muscle tissue features comprising:
    a fiber bundle support for applying a lifting force to a fiber bundle that has been pulled away from the body of a muscle, the fiber bundle support having an initial length to lift the fiber bundle a lifting distance;
    an image capture system for viewing the illuminated portion of the lifted fiber bundle;
    a force transducer for measuring the lifting force applied by the fiber bundle support;
    a position sensor for measuring the lifting distance of the fiber bundle to which a lifting force has been applied; and
    a routine for calculating the axial tension on the fiber bundle based on the initial length, the lifting force applied to the fiber bundle and the lifting distance.

* * * * *